US012697066B2

(12) United States Patent
Kwak et al.

(10) Patent No.: US 12,697,066 B2
(45) Date of Patent: Aug. 4, 2026

(54) BIOMETRIC SENSOR INTEGRATED WITH ELECTRONIC DISPLAY OF A WEARABLE DEVICE

(71) Applicant: Fitbit LLC, San Francisco, CA (US)

(72) Inventors: Dong Yeung Kwak, San Jose, CA (US); Triton Hurd, Encinitas, CA (US); Jens Mitchell Nielsen, San Francisco, CA (US); Steven Thomas Woodward, Fremont, CA (US); Chih-Chun Chang, Hsinchu City (TW); Gang Cheng, Burlingame, CA (US); Dennis Jisung Kim, Milpitas, CA (US); Mike Suk, Palo Alto, CA (US); Brian Dennis Paschke, San Francisco, CA (US); Cody David Lee, San Diego, CA (US); Jeffrey Michael Borra, San Diego, CA (US); Ritu Verma, San Diego, CA (US); Pieris Berreitter, San Francisco, CA (US)

(73) Assignee: FITBIT, LLC, San Francisco, CA (US)

( * ) Notice: Subject to any disclaimer, the term of this patent is extended or adjusted under 35 U.S.C. 154(b) by 737 days.

(21) Appl. No.: 18/013,717

(22) PCT Filed: Jul. 19, 2021

(86) PCT No.: PCT/US2021/042169
§ 371 (c)(1),
(2) Date: Dec. 29, 2022

(87) PCT Pub. No.: WO2023/003529
PCT Pub. Date: Jan. 26, 2023

(65) Prior Publication Data
US 2023/0255559 A1 Aug. 17, 2023

(51) Int. Cl.
*A61B 5/024* (2006.01)
*A61B 5/00* (2006.01)
(Continued)

(52) U.S. Cl.
CPC .............. *A61B 5/681* (2013.01); *A61B 5/256* (2021.01); *A61B 2560/0468* (2013.01); *A61B 2562/166* (2013.01)

(58) Field of Classification Search
CPC . A61B 5/681; A61B 5/256; A61B 2560/0468; A61B 2562/166;
(Continued)

(56) References Cited

U.S. PATENT DOCUMENTS 11,122,688 B2 * 9/2021 Chong Rodriguez ...................... A61B 5/02055
2015/0141784 A1 * 5/2015 Morun .................... G06F 3/014 427/79
(Continued)

FOREIGN PATENT DOCUMENTS

EP 3626159 3/2020

OTHER PUBLICATIONS

Chinese Search Report Corresponding to Application No. 2021800463389 on May 14, 2025.
(Continued)

*Primary Examiner* — Carl H Layno
*Assistant Examiner* — Anh-Khoa N Dinh
(74) *Attorney, Agent, or Firm* — DORITY & MANNING P.A.

(57) ABSTRACT

A wearable computing device includes an outer covering defining an outer-most top surface and an outer perimeter and an internal volume defined, at least in part, by an inner surface of the outer covering. The wearable computing device also includes an electronic display and an electronic
(Continued)

display module connector arranged within the internal volume. Further, the wearable computing device includes at least one biometric sensor electrode positioned on the outermost top surface of the outer covering and wrapping around one or more side edges of the outer covering to the internal volume. Moreover, the wearable computing device includes a printed circuit board arranged within the internal volume. In addition, the wearable computing device includes a conductive component electrically connecting the biometric sensor electrode(s) to the printed circuit board through the electronic display module connector.

18 Claims, 14 Drawing Sheets

(51) Int. Cl.
|  |  |
| --- | --- |
| *A61B 5/0531* | (2021.01) |
| *A61B 5/256* | (2021.01) |
| *A61B 5/28* | (2021.01) |

(58) Field of Classification Search
CPC ............ A61B 5/02438; A61B 5/02444; A61B 5/0245; A61B 2562/0209; A61B 2562/16; A61B 2503/10; A61B 2562/125; A61B 5/0531; A61B 5/28; A61B 2562/227; A61B 8/085; A61B 90/30; A61B 10/0051; A61B 17/07292; A61B 17/1155; A61B 2017/00216; A61B 2017/00809; A61B 2017/00818; A61B 2050/3014; A61B 2090/0804; A61B 2503/12; A61B 2503/22; A61B 2560/0228; A61B 2560/04; A61B 2562/24; A61B 2562/242; A61B 2576/026; A61B 5/0042; A61B 5/0082; A61B 5/02455; A61B 5/0823; G06F 1/1656; G06F 1/1658; G06F 1/163; G06F 1/1643; G06F 1/1684
See application file for complete search history.

(56) References Cited

U.S. PATENT DOCUMENTS

| | | | |
| --- | --- | --- | --- |
| 2016/0058375 A1* | 3/2016 | Rothkopf | ............. G04G 21/025 |
| | | | 600/323 |
| 2016/0062417 A1* | 3/2016 | Chu | ........................ A61B 5/681 |
| | | | 361/679.03 |
| 2016/0064804 A1 | 3/2016 | Kim et al. | |
| 2017/0011210 A1* | 1/2017 | Cheong | .................. A61B 5/681 |
| 2017/0296088 A1 | 10/2017 | Choi | |
| 2018/0220972 A1* | 8/2018 | Jeong | ................... A61B 5/7475 |
| 2018/0235542 A1 | 8/2018 | Yun et al. | |
| 2020/0128670 A1* | 4/2020 | Chong Rodriguez | . A61B 5/329 |
| 2020/0196883 A1* | 6/2020 | Matsumoto | .......... A61B 5/0295 |
| 2020/0323489 A1 | 10/2020 | Kim et al. | |
| 2021/0015388 A1 | 1/2021 | Kim et al. | |
| 2021/0030359 A1 | 2/2021 | Jeong et al. | |
| 2021/0159651 A1 | 5/2021 | Ryu et al. | |

OTHER PUBLICATIONS

International Search Report for Application No. PCT/ US2021/042169, mailed on Apr. 21, 2022, 6 pages.
International Preliminary Report on Patentability for Application No. PCT/US2021/042169, mailed Feb. 1, 2024, 9 pages.

* cited by examiner

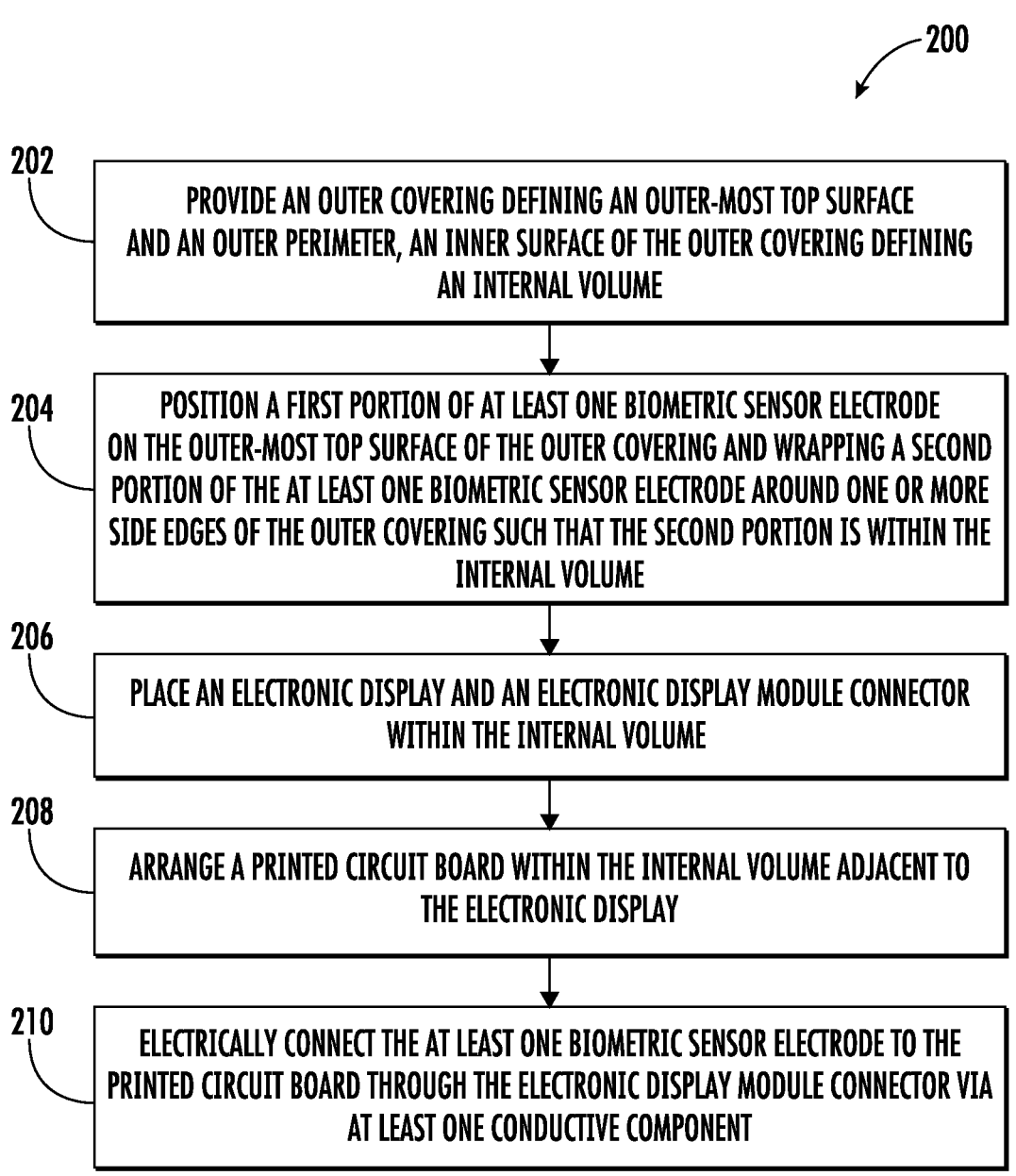

—200

202

PROVIDE AN OUTER COVERING DEFINING AN OUTER-MOST TOP SURFACE AND AN OUTER PERIMETER, AN INNER SURFACE OF THE OUTER COVERING DEFINING AN INTERNAL VOLUME

204

POSITION A FIRST PORTION OF AT LEAST ONE BIOMETRIC SENSOR ELECTRODE ON THE OUTER-MOST TOP SURFACE OF THE OUTER COVERING AND WRAPPING A SECOND PORTION OF THE AT LEAST ONE BIOMETRIC SENSOR ELECTRODE AROUND ONE OR MORE SIDE EDGES OF THE OUTER COVERING SUCH THAT THE SECOND PORTION IS WITHIN THE INTERNAL VOLUME

206

PLACE AN ELECTRONIC DISPLAY AND AN ELECTRONIC DISPLAY MODULE CONNECTOR WITHIN THE INTERNAL VOLUME

208

ARRANGE A PRINTED CIRCUIT BOARD WITHIN THE INTERNAL VOLUME ADJACENT TO THE ELECTRONIC DISPLAY

210

ELECTRICALLY CONNECT THE AT LEAST ONE BIOMETRIC SENSOR ELECTRODE TO THE PRINTED CIRCUIT BOARD THROUGH THE ELECTRONIC DISPLAY MODULE CONNECTOR VIA AT LEAST ONE CONDUCTIVE COMPONENT

FIG. 24

BIOMETRIC SENSOR INTEGRATED WITH ELECTRONIC DISPLAY OF A WEARABLE DEVICE

CROSS-REFERENCE TO RELATED APPLICATIONS

The present application is based upon and claims the right of priority under 35 U.S.C. § 371 to International Application No. PCT/US2021/042169 filed on Jul. 19, 2021, which is incorporated by reference herein.

FIELD

The present disclosure relates generally to wearable computing devices, and more particularly, to a biometric sensor electrode integrated in the top surface of the covering of a wearable computing device, thereby providing increased surface area and improved signal quality of the sensor.

BACKGROUND

Recent consumer interest in personal health has led to a variety of personal health monitoring devices being offered on the market. Recent advances in sensor, electronics, and power source miniaturization have allowed the size of personal health monitoring devices, also referred to herein as "biometric tracking" or "biometric monitoring" devices, to be offered in extremely small sizes that were previously impractical.

These biometric monitoring devices may collect, derive, and/or provide one or more of the following types of information: heart rate, calorie burn, floors climbed and/or descended, location and/or heading, elevation, ambulatory speed and/or distance traveled, etc. For a wearable computing device, the front or top surface is typically occupied by a large electronic display, often covered with an optically clear covering constructed of certain materials (such as glass, polycarbonate, acrylic, etc.). This covering often requires a seal around its perimeter, making the electronic display covering larger than the active region of the electronic display itself.

Accordingly, the present disclosure is related to a biometric sensor electrode integrated in the top surface of the covering of such wearable computing devices, thereby providing increased surface area and improved signal quality of the sensor. By integrating the biometric sensor electrode onto the covering, the user is able to access the sensor in a more ergonomic manner, allowing the user to make contact with a variety of extremities (palm, fingers, leg, etc.) without requiring high dexterity on a small surface.

SUMMARY

Aspects and advantages of embodiments of the present disclosure will be set forth in part in the following description, or can be learned from the description, or can be learned through practice of the embodiments.

One example aspect of the present disclosure is directed to a wearable computing device. The wearable computing device includes an outer covering defining an outer-most top surface and an outer perimeter and an internal volume defined, at least in part, by an inner surface of the outer covering. The wearable computing device also includes an electronic display and an electronic display module connector arranged within the internal volume. Further, the wearable computing device includes at least one biometric sensor electrode positioned on the outer-most top surface of the outer covering and wrapping around one or more side edges of the outer covering to the internal volume. Moreover, the wearable computing device includes a printed circuit board arranged within the internal volume. In addition, the wearable computing device includes a conductive component electrically connecting the biometric sensor electrode(s) to the printed circuit board through the electronic display module connector. Further, the conductive component defines a low-resistance path.

Another example aspect of the present disclosure is directed to a method of assembling a wearable computing device. The method includes providing an outer covering defining an outer-most top surface and an outer perimeter, an inner surface of the outer covering defining an internal volume. The method also includes positioning a first portion of at least one biometric sensor electrode on the outer-most top surface of the outer covering and wrapping a second portion of the at least one biometric sensor electrode around one or more side edges of the outer covering such that the second portion is within the internal volume. Further, the method includes placing an electronic display and an electronic display module connector within the internal volume. Moreover, the method includes arranging a printed circuit board within the internal volume adjacent to the electronic display. In addition, the method includes electrically connecting the biometric sensor electrode(s) to the printed circuit board through the electronic display module connector via at least one conductive component. Further, the conductive component(s) defines a low-resistance path.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which:

FIG. 24 provides a flow chart illustrating one embodiment of a method of assembling a wearable computing device according to the present disclosure.

DETAILED DESCRIPTION

Figure 1:
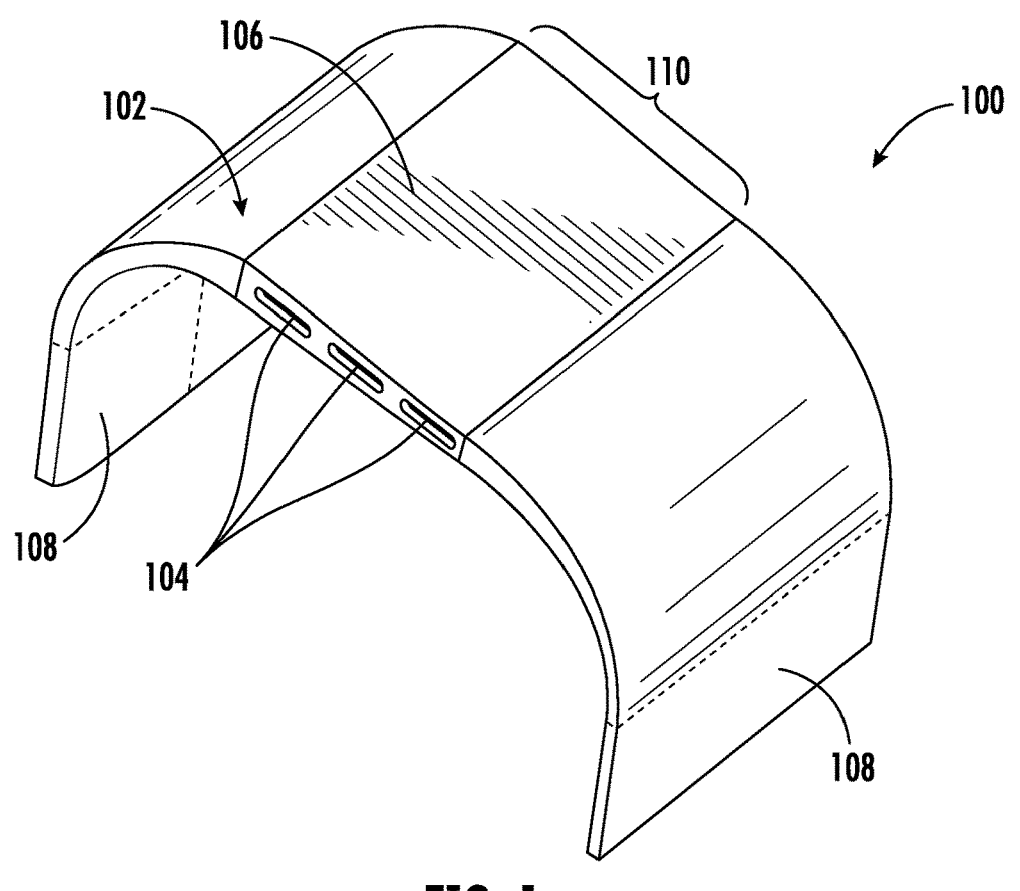
FIG. 1 provides a perspective view of a wearable computing device according to one embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Overview

For a wearable computing device, the front or top surface is typically occupied by a large electronic display, often covered with an optically clear covering constructed of certain materials (such as glass, polycarbonate, acrylic, etc.). This covering often requires a seal around its perimeter, making the electronic display covering larger than the active region of the electronic display itself. Accordingly, the present disclosure is related to a biometric sensor electrode integrated in the top surface of the covering on a wearable computing device, thereby providing increased surface area and improved signal quality of the sensor. By integrating the biometric sensor electrode onto the covering, the user is able to access the sensor in a more ergonomic manner, allowing the user to make contact with a variety of extremities (palm, fingers, leg, etc.) without requiring high dexterity on a small surface.

To activate the biometric sensor electrode created on the top surface of the covering, the sensor requires electrically connecting the sensor to the sense hub (which contains the main circuit) in the system board within the wearable computing device. Thus, the present disclosure is also directed to an improved conductive component between the biometric sensor electrode and the main circuit of the wearable computing device. As such, the present disclosure provides for electrically connecting an efficient and effective conductive component to a printed or flexible circuit board through the electronic display module and into the main circuit of the wearable computing device. In particular, the improved conductive component of the present disclosure has a low feed-thru electrical resistance and does not require extra space. Moreover, the integrated biometric sensor electrode allows for an easy assembly process without increasing costs or reducing reliability.

For example, in an embodiment, a direct/indirect connection may be used with conductive foam and an adhesive (such as anisotropic conductive film (ACF) and silver epoxy). In such an embodiment, physical vapor deposition (PVD) contact pads are positioned on the top surface and sandwiched between the sensor metal bottom of the covering and the top surface of the electronic display module. Next, a low-resistance conductive foam is placed between the sensor metal bottom and the PVD contact pads to connect the biometric sensor electrode to PVD contact pad(s). Further, the PVD contact pad(s) on the top surface is connected to a flexible printed circuit (FBC) through the electronic display module connector. The FBC is bonded on the top surface using an adhesive, such as ACF, by conventional FPC bonding processes. Moreover, the electronic display module connector is secured to the main device body, where the main circuit is located.

In particular, by providing a conductive component between the biometric sensor electrode and the main circuit of the wearable computing device, it is e.g., possible to obtain a compact and robust design of the wearable computing.

With reference now to the Figures, example embodiments of the present disclosure will be discussed in further detail.

Example Devices and Systems

Referring now to the drawings, FIG. 1 illustrates a perspective view of a wearable computing device 100 according to the present disclosure. In particular, as shown, the wearable computing device 100 may be worn on a person's forearm like a wristwatch. In addition, as shown, the wearable computing device 100 has a housing 102 that contains the electronics associated with the wearable computing device 100. Further, as shown, the wearable computing device 100 includes one or more buttons 104 and an electronic display 106 that is accessible/visible through the housing 102. In some embodiments, for example, the button(s) 404 may be implemented to provide a mechanism to activate a heart rate sensor to collect heart rate data. Moreover, in an embodiment, the electronic display 106 may cover an electronics package 110 (also referred to herein as an electronic display module connector), which is also housed with the housing 102. In addition, as shown, a wristband 108 may be integrated with the housing 102.

Figure 2:
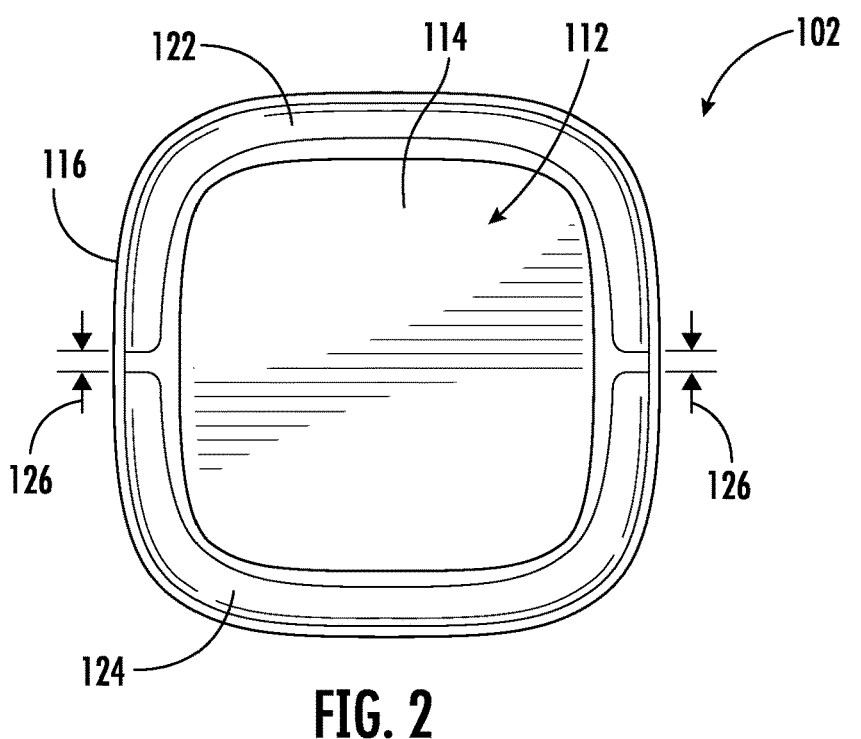
FIG. 2 provides a top view of the display of the wearable computing device of FIG. 1.
Figure 3:
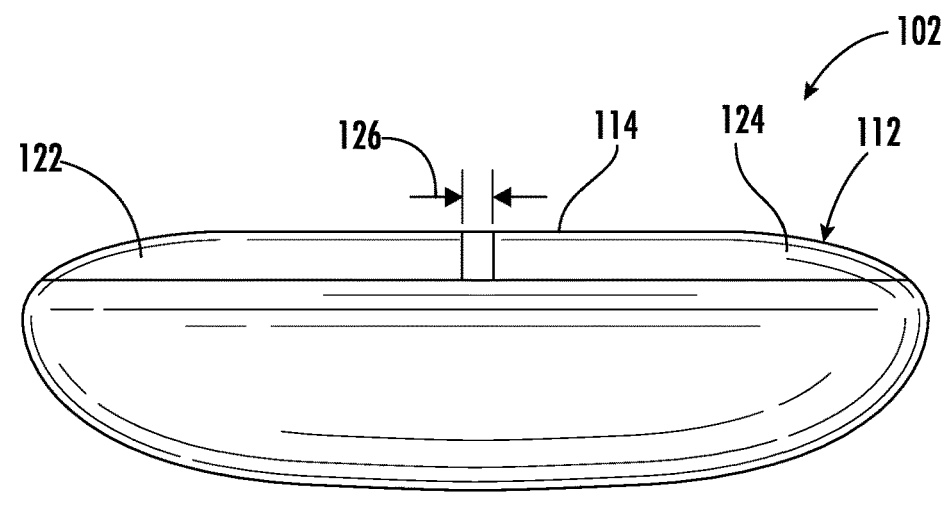
FIG. 3 provides a side view of the display of the wearable computing device of FIG. 1.
Figure 4:
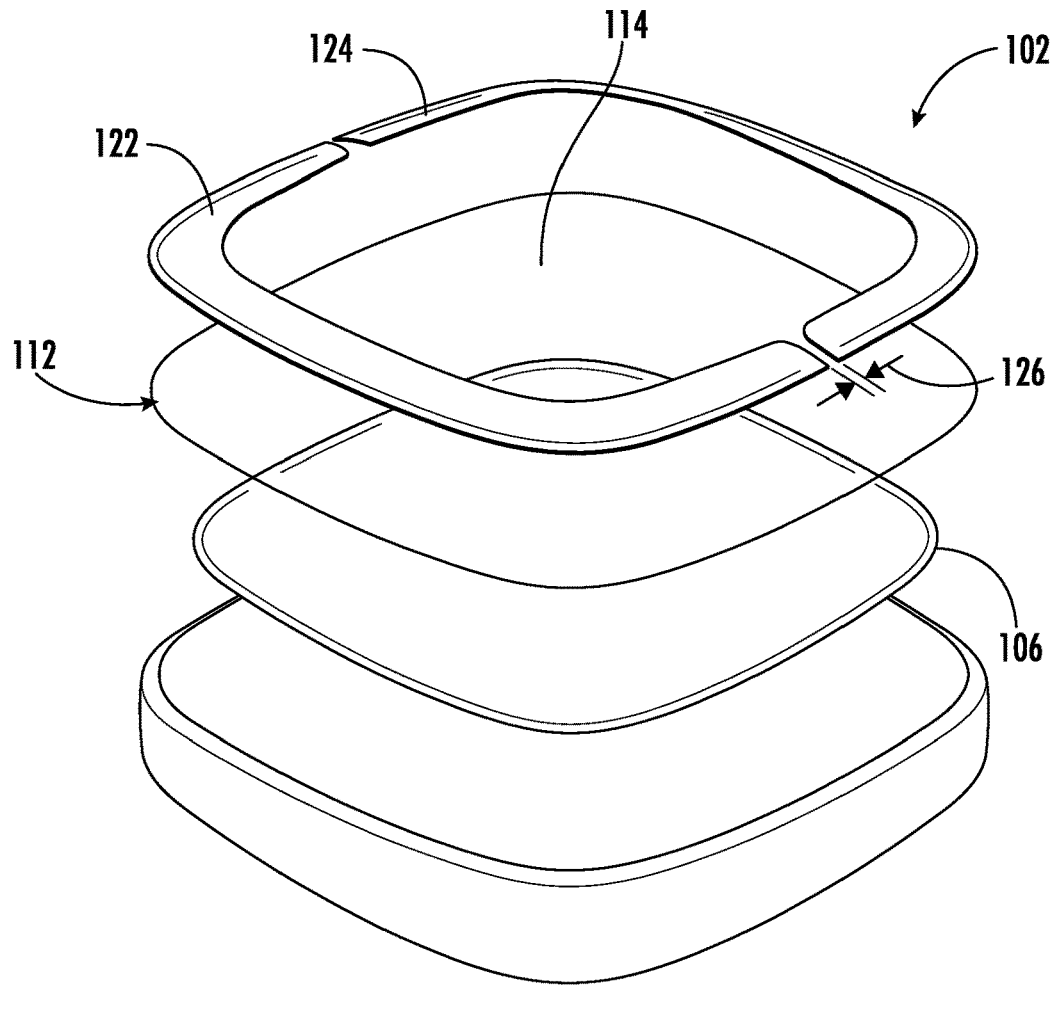
FIG. 4 provides an exploded view of the display of the wearable computing device of FIG. 1.
Figure 5:
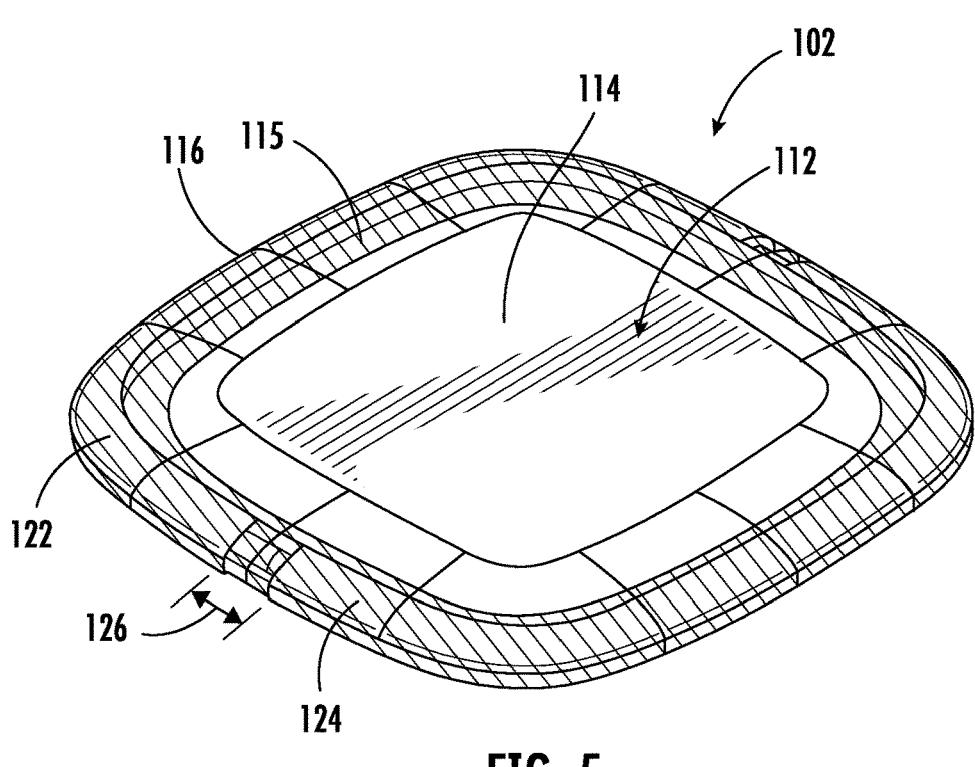
FIG. 5 provides a transparent, top, perspective view of the display of the wearable computing device of FIG. 1.
Figure 6:
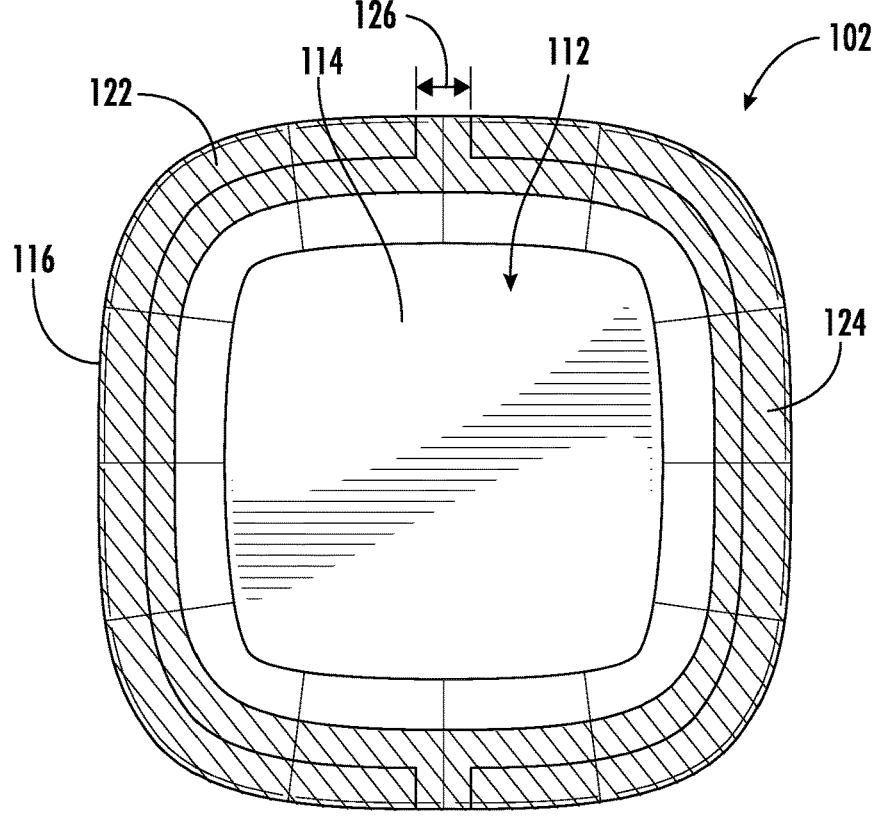
FIG. 6 provides a transparent, top view of the display of the wearable computing device of FIG. 1.
Figure 7:
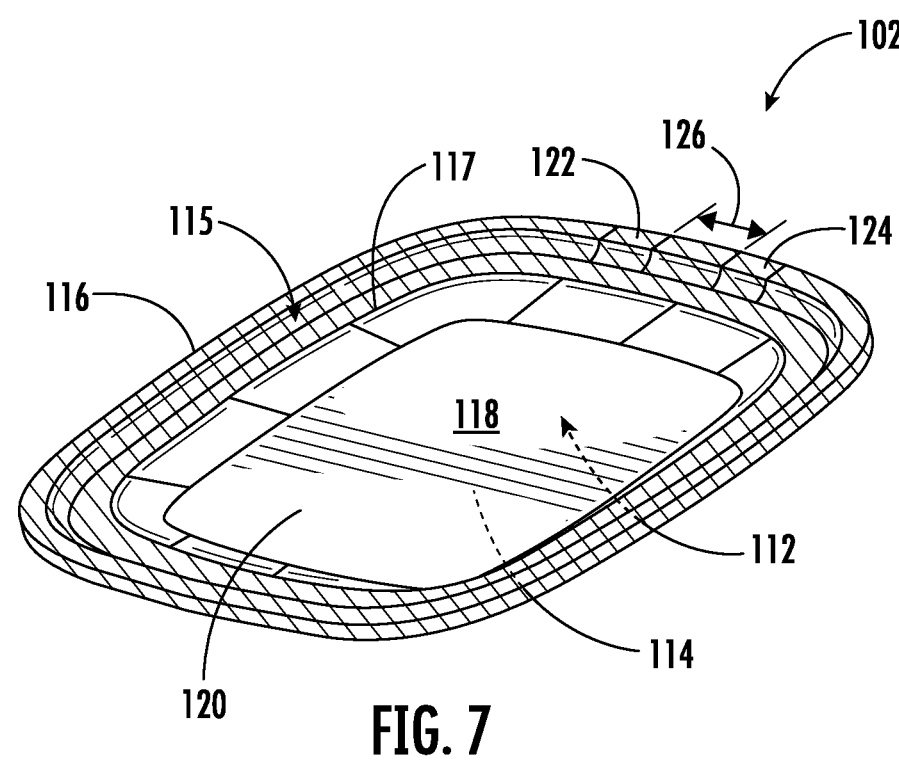
FIG. 7 provides a transparent, bottom, perspective view of the display of the wearable computing device of FIG. 1.
Figure 8:
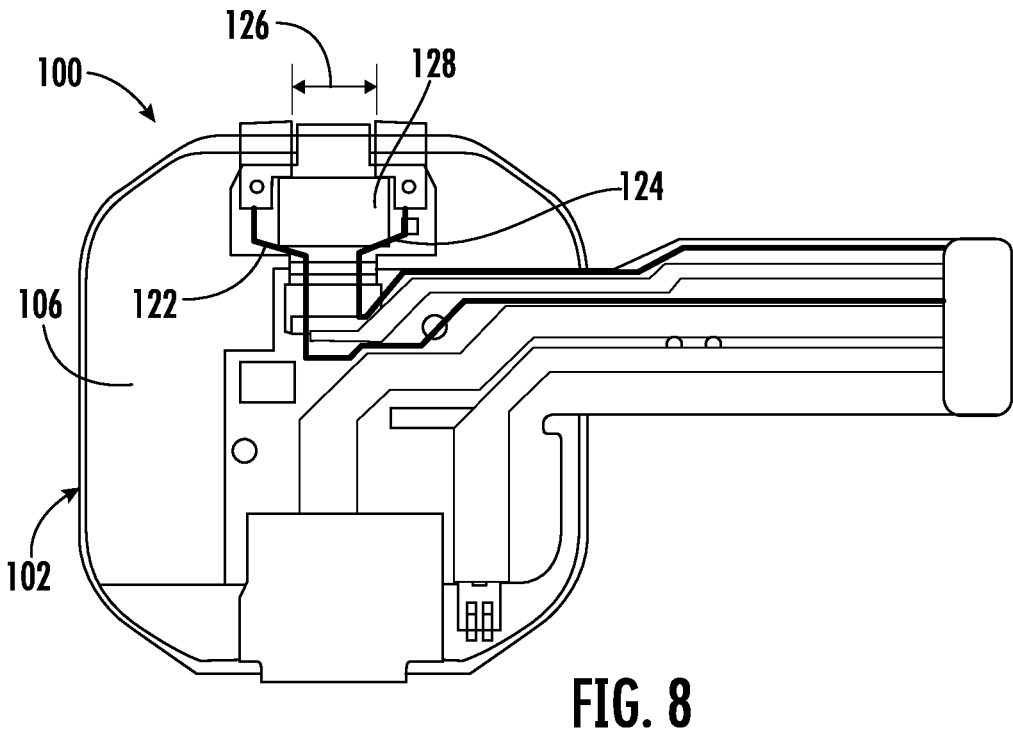
FIG. 8 provides a schematic view of various electrical connections of the display of the wearable computing device of FIG. 1.

Referring now to FIGS. 2-7, various views of the housing 102 of the wearable computing device 100 according to the present disclosure are illustrated. In particular, FIG. 2 illustrates a top view of one embodiment of the housing 102 according to the present disclosure; FIG. 3 illustrates a side view of one embodiment of the housing 102 according to the present disclosure; FIG. 4 illustrates an exploded side view of one embodiment of the housing 102 according to the present disclosure; FIG. 5 illustrates a transparent, perspective view of one embodiment of the housing 102 according to the present disclosure; FIG. 6 illustrates a transparent, top view of one embodiment of the housing 102 according to the present disclosure; FIG. 7 illustrates a transparent, perspective view of one embodiment of the housing 102 according to the present disclosure; and FIG. 8 illustrates a rear view of one embodiment of the electronics package 110 within the housing 102 according to the present disclosure.

Furthermore, as shown generally in FIGS. 2-7, the housing 102 includes an outer covering 112 defining an outer-most top surface 114 and an outer perimeter 116. For example, in an embodiment, the outer covering 112 may be constructed of glass, polycarbonate, acrylic, or similar. Thus, as shown particularly in FIG. 7, an internal volume 118 is defined, at least in part, by an inner surface 120 of the outer covering 112. In addition, as shown in FIGS. 5 and 7, the wearable computing device 100 may also include a seal 115 arranged along the outer perimeter 116 of the outer covering 112. Thus, in such embodiments, as shown in FIG. 7, the internal volume 118 is defined by the inner surface 120 of the outer covering 112 and an inner edge 117 of the seal 115. Accordingly, as shown, the electronic display 106 and the electronic display module connector 110 may be arranged within the internal volume 118, as further described herein.

In addition, as shown in FIGS. 2-7, the wearable computing device 100 further includes at least one biometric sensor electrode, such as a first biometric sensor electrode 122 and a second biometric sensor electrode 124, positioned on the outer-most top surface 114 of the outer covering 112 and wrapping around one or more side edges of the outer covering 112 to the internal volume 118 (see e.g., FIG. 7). Thus, as shown, in an embodiment, the wearable computing device 100 may include two sensor electrodes 122, 124 placed in a pair. In such embodiment, the two sensor electrodes 122, 124 may have an overlapped space over a display dimension.

For example, as shown in FIG. 7, in an embodiment, the biometric sensor electrode(s) 122, 124 wrap around the side edge of the outer covering 112 and the inner edge 117 of the seal 115 to the internal volume 118. Furthermore, in such embodiments, as shown generally in FIGS. 2-7, the first and second biometric sensor electrodes 122, 124 may also be spaced apart by one or more gaps 126. More specifically, as shown in FIG. 2, the first and second biometric sensor electrodes 122, 124 may be spaced apart via multiple gaps 126 on opposing sides of the outer covering 112. In other words, as shown, the two sensor electrodes 122, 124 may have space in the middle to avoid the printed circuit board bonding area.

Figure 12:
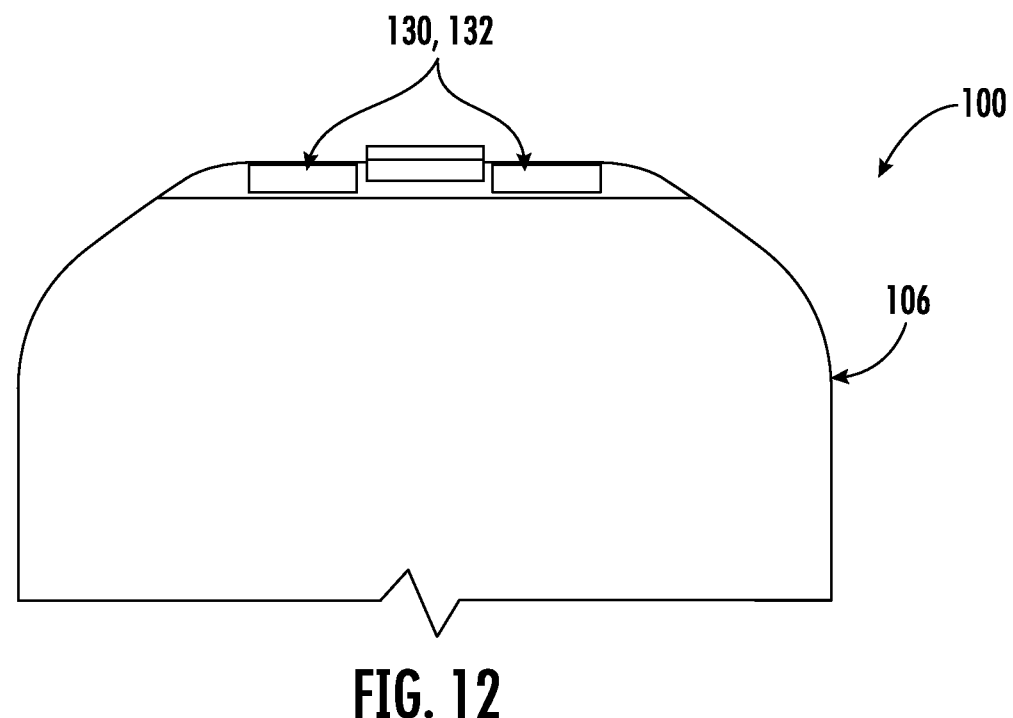
FIG. 12 provides top view of the double-side conductive tape or the double-side conductive foam arranged on the electronic display of the wearable computing device according to one embodiment of the present disclosure.
Figure 13:
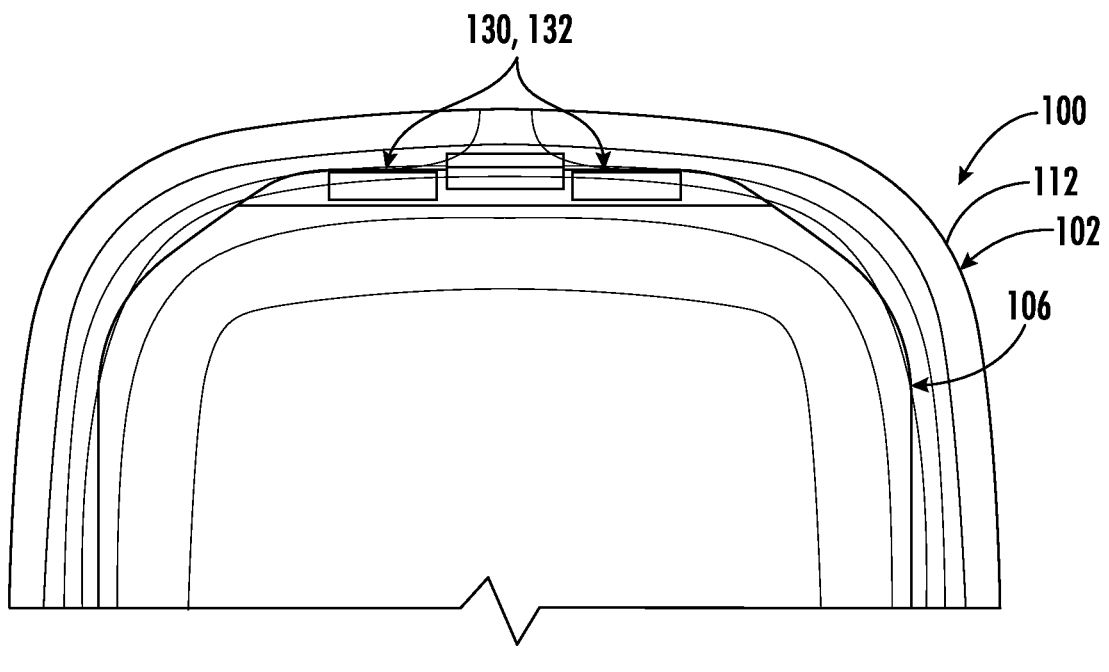
FIG. 13 provides top view of the wearable computing device according to one embodiment of the present disclosure, particularly illustrating double-side conductive tape or foam arranged on the electronic display of the wearable computing device.
Figure 18:
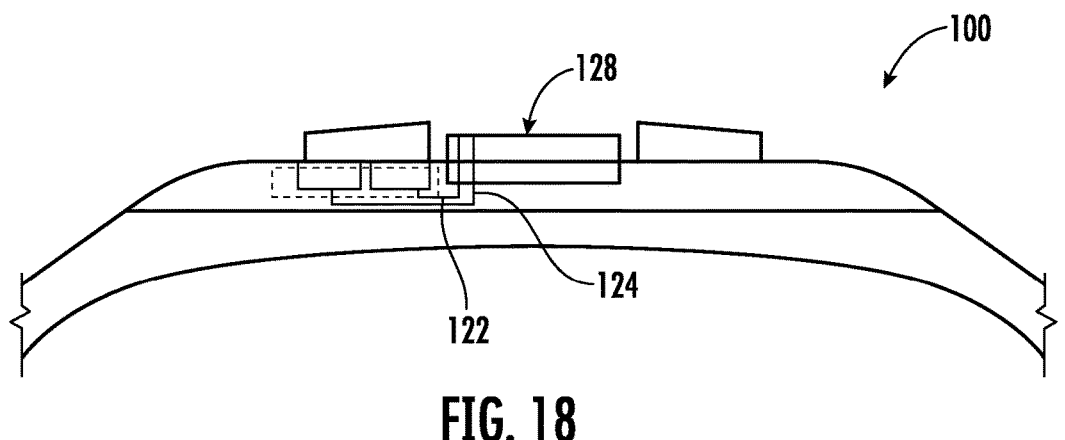
FIG. 18 provides a cross-sectional view of the wearable computing device according to one embodiment of the present disclosure, particularly illustrating first and second biometric sensor electrodes arranged on the same side of a printed circuit board.

Moreover, as shown in FIG. 8, the wearable computing device 100 includes a printed circuit board 128 arranged within the internal volume 118, i.e., on a rear side of the electronics display 106. Thus, in an embodiment, as shown in FIGS. 8 and 12, the first and second biometric sensor electrodes 122, 124 are arranged on opposite sides of the printed circuit board 128. Alternatively, as shown in FIG. 18, the first and second biometric sensor electrodes 122, 124 are arranged on the same side of the printed circuit board 128. Furthermore, in certain embodiments, the biometric sensor electrode(s) 122, 124 described herein may each include a physical vapor deposition (PVD) sensor pad. In addition, in an embodiment, the biometric sensor electrode(s) 122, 124 described herein may include an electrocardiogram (ECG) sensor, an electrodermal activity (EDA) sensor, or any other suitable sensor type.

Figure 9:
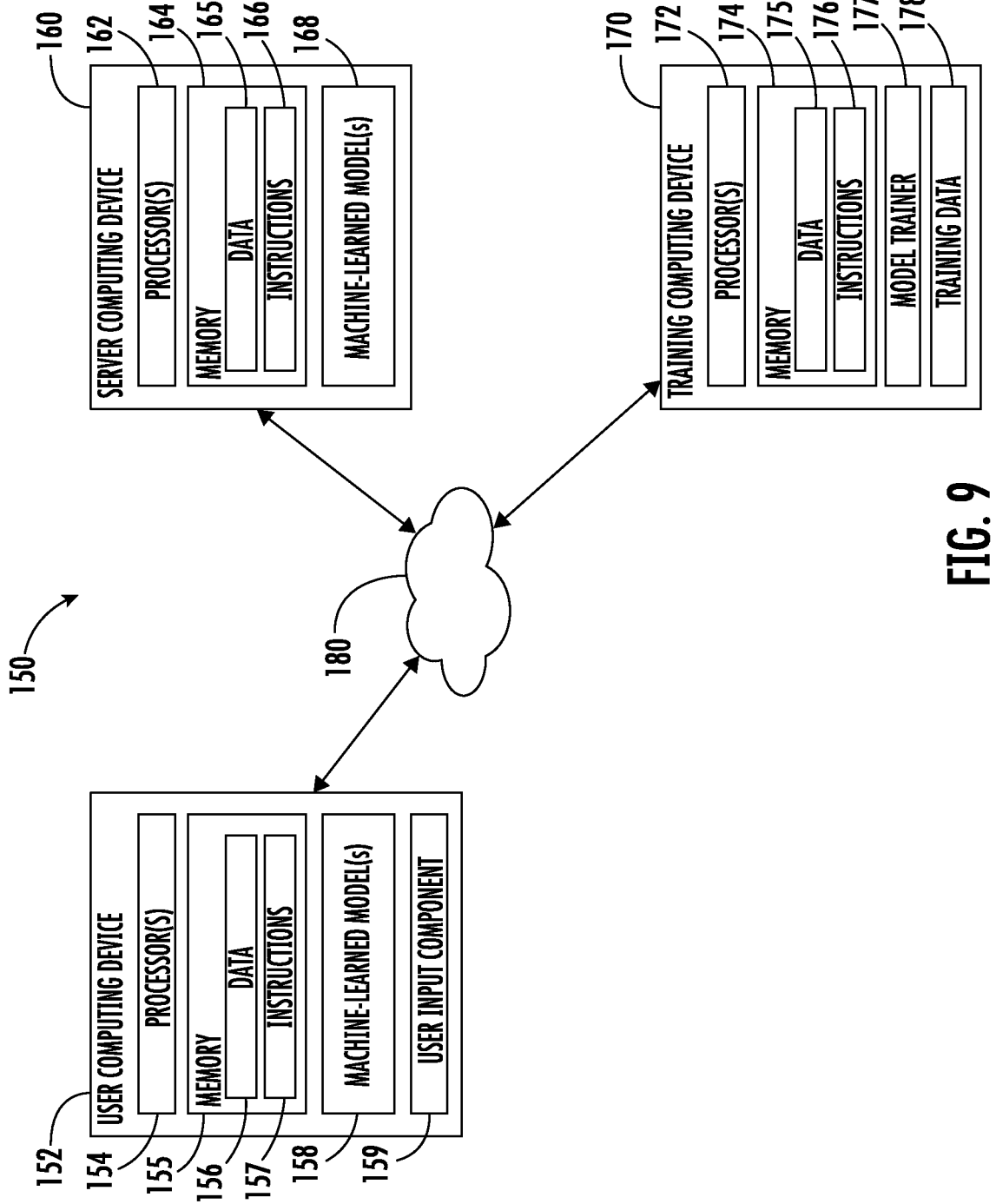
FIG. 9 provides a block diagram of an example computing system for a wearable computing device according to one embodiment of the present disclosure.

Accordingly, the biometric sensor electrode(s) 122, 124 described herein may be connected through inter-media materials to the electronic display module connector 110, which may include a computing system configured to operate the wearable computing device 100. In particular, as shown in FIG. 9, a block diagram of an example computing system 150 according to example embodiments of the present disclosure is illustrated. Further, as shown, in an embodiment, the computing system 150 includes a user computing device 152, a server computing system 160, and a training computing system 170 that are communicatively coupled over a network 180. Thus, in an embodiment, components of the user computing device 152 may be part of the wearable computing device 100.

In particular, as shown, the user computing device 152 includes one or more processors 154 and a memory 155. The one or more processors 154 can be any suitable processing device (e.g., a processor core, a microprocessor, an ASIC, an FPGA, a controller, a microcontroller, etc.) and can be one processor or a plurality of processors that are operatively connected. The memory 155 can include one or more non-transitory computer-readable storage media, such as RAM, ROM, EEPROM, EPROM, flash memory devices, magnetic disks, etc., and combinations thereof. The memory 155 can store data 156 and instructions 157 which are executed by the processor 154 to cause the user computing device 152 to perform operations.

In some implementations, the user computing device 152 can store or include one or more models 158. For example, in an embodiment, the model(s) 158 can be or can otherwise include various machine-learned models such as neural networks (e.g., deep neural networks) or other types of machine-learned models, including non-linear models and/ or linear models. Neural networks can include feed-forward neural networks, recurrent neural networks (e.g., long short-term memory recurrent neural networks), convolutional neural networks or other forms of neural networks.

Thus, in some implementations, the model(s) 158 can be received from the server computing system 160 over the network 180, stored in the user computing device memory 155, and then used or otherwise implemented by the processor(s) 154. Additionally, or alternatively, one or more models 168 can be included in or otherwise stored and implemented by the server computing system 160 that communicates with the user computing device 152 according to a client-server relationship. Thus, the model(s) 158 can be stored and implemented at the user computing device 152 and/or the model(s) 168 can be stored and implemented at the server computing system 160.

The user computing device 152 can also include one or more user input components 159 that receives user input. For example, the user input component 159 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input.

The server computing system 160 can be any type of computing device, such as, for example, a personal computing device (e.g., laptop or desktop), a mobile computing device (e.g., smartphone or tablet), a gaming console or controller, a wearable computing device, an embedded computing device, or any other type of computing device. Further, as shown, the server computing system 160 includes one or more processors 162 and a memory 164. The processor(s) 162 can be any suitable processing device (e.g., a processor core, a microprocessor, an ASIC, an FPGA, a controller, a microcontroller, etc.) and can be one processor or a plurality of processors that are operatively connected. The memory 164 can include one or more non-transitory computer-readable storage media, such as RAM, ROM, EEPROM, EPROM, flash memory devices, magnetic disks, etc., and combinations thereof. The memory 164 can store data 165 and instructions 166 which are executed by the processor 162 to cause the server computing system 160 to perform operations.

In some implementations, the server computing system 160 includes or is otherwise implemented by one or more server computing devices. In instances in which the server computing system 160 includes plural server computing devices, such server computing devices can operate according to sequential computing architectures, parallel computing architectures, or some combination thereof.

As described above, the server computing system 160 can store or otherwise include one or more models 168. For example, the model(s) 168 can be or can otherwise include various machine-learned models. Example machine-learned models include neural networks or other multi-layer non-linear models. Example neural networks include feed-forward neural networks, deep neural networks, recurrent neural networks, and convolutional neural networks.

The user computing device 152 and/or the server computing system 160 can train the models 158 and/or 168 via interaction with the training computing system 170 that is communicatively coupled over the network 180. The training computing system 170 can be separate from the server computing system 160 or can be a portion of the server computing system 160.

The training computing system 170 includes one or more processors 172 and a memory 174. The processor(s) 172 can be any suitable processing device (e.g., a processor core, a microprocessor, an ASIC, an FPGA, a controller, a microcontroller, etc.) and can be one processor or a plurality of processors that are operatively connected. The memory 174 can include one or more non-transitory computer-readable storage media, such as RAM, ROM, EEPROM, EPROM, flash memory devices, magnetic disks, etc., and combinations thereof. The memory 174 can store data 175 and instructions 176 which are executed by the processor 172 to cause the training computing system 170 to perform operations. In some implementations, the training computing system 170 includes or is otherwise implemented by one or more server computing devices. The training computing system 170 can also include a model trainer 177 that trains the machine-learned models 158 and/or 168 stored at the user computing device 152 and/or the server computing system 160 using various training or learning techniques. In particular, in an embodiment, the model trainer 177 can train the models 158 and/or 168 based on a set of training data 178.

The model trainer 177 includes computer logic utilized to provide desired functionality. The model trainer 177 can be implemented in hardware, firmware, and/or software controlling a general purpose processor. For example, in some implementations, the model trainer 177 includes program files stored on a storage device, loaded into a memory and executed by one or more processors. In other implementations, the model trainer 177 includes one or more sets of computer-executable instructions that are stored in a tangible computer-readable storage medium such as RAM, hard disk, or optical or magnetic media.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

Referring now to FIGS. 10-20, the wearable computing device 100 of the present disclosure further includes a conductive component 130 electrically connecting the biometric sensor electrode(s) 122, 124 to the printed circuit board 128 through the electronic display module connector 110. In particular, the conductive component 130 described herein provides a low-resistance path (e.g., on the order of less than about 50 Ohms, in particular less than 10 Ohms).

Figure 10:
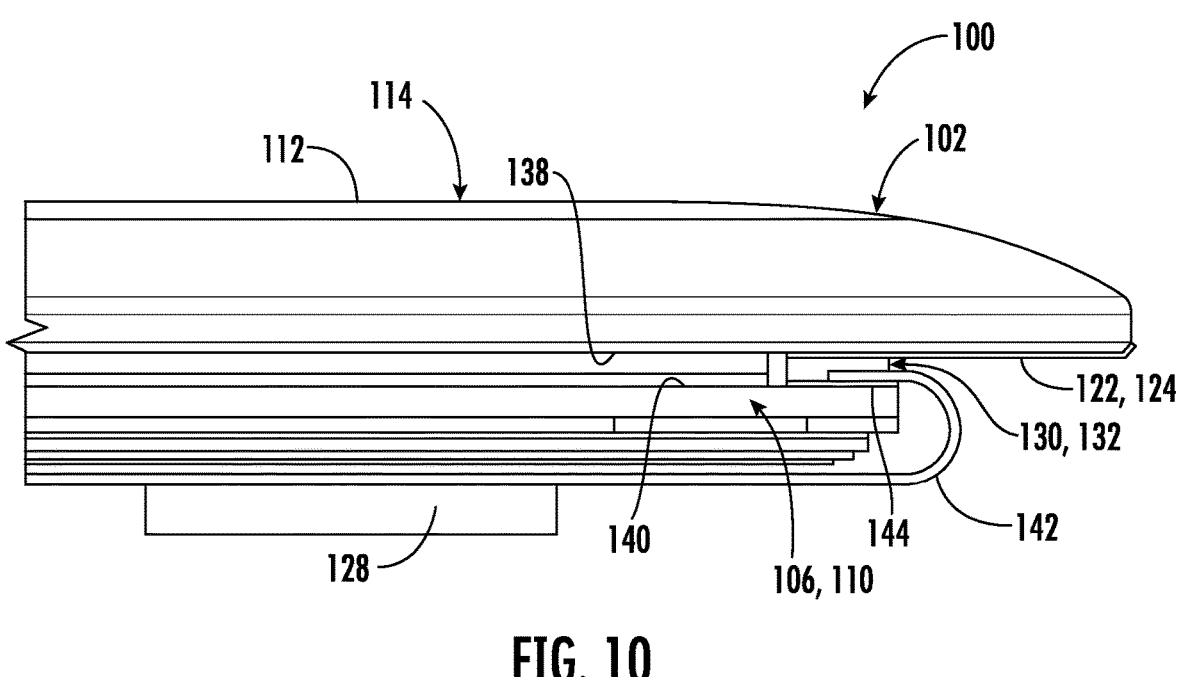
FIG. 10 provides a side view of a two-dimensional wearable computing device according to one embodiment of the present disclosure, particularly illustrating a double-side conductive tape or double-side conductive foam electrically connecting a biometric sensor electrode partly on an outermost top surface of the outer covering and partly on an inner surface of the outer covering to a printed or flexible circuit board through the electronic display module connector.
Figure 11:
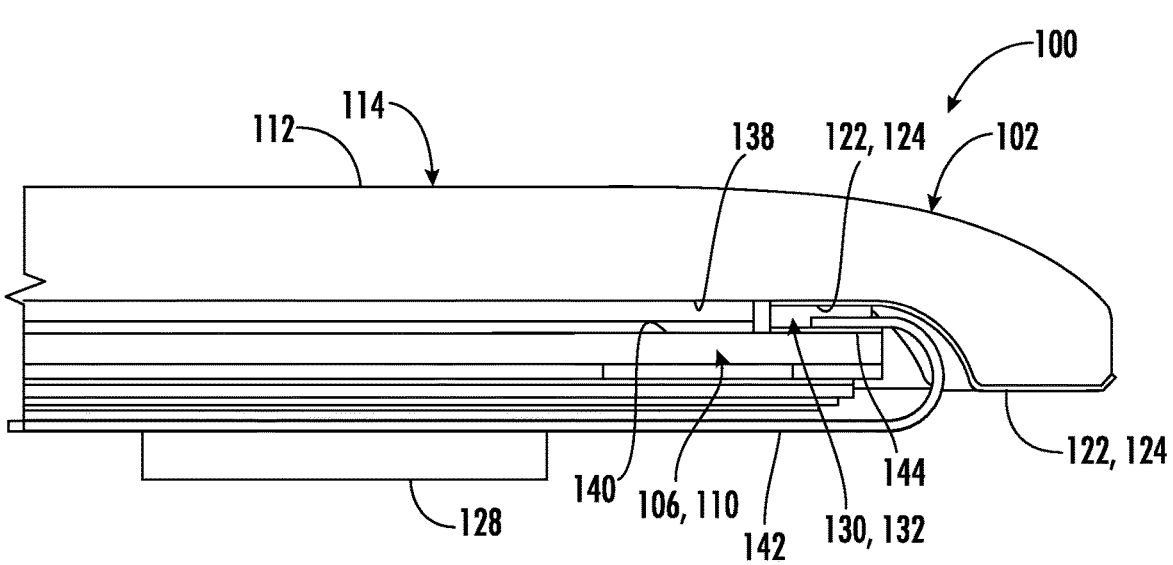
FIG. 11 provides a side view of a three-dimensional wearable computing device according to one embodiment of the present disclosure, particularly illustrating a double-side conductive tape or double-side conductive foam electrically connecting a biometric sensor electrode partly on an outermost top surface of the outer covering and partly on an inner surface of the outer covering to a printed or flexible circuit board through the electronic display module connector.
Figure 14:
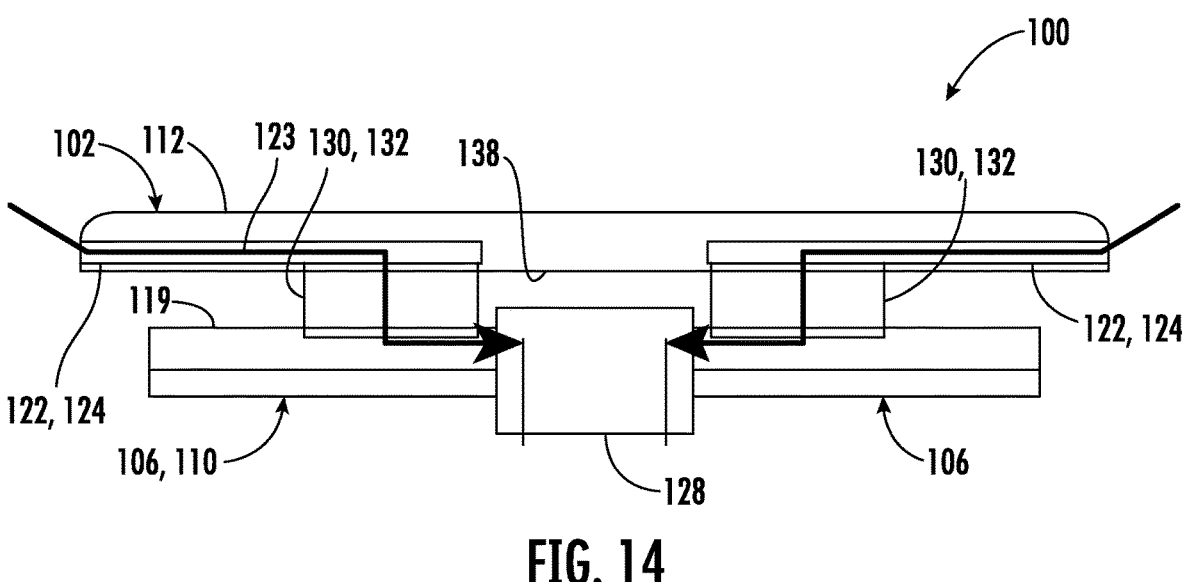
FIG. 14 provides a cross-sectional view of the wearable computing device according to one embodiment of the present disclosure, particularly illustrating first and second biometric sensor electrodes arranged on opposite sides of a printed circuit board and arranged between a bottom surface of the outer covering and a top surface of the electronic display.

More specifically, as shown in FIGS. 10-17, the conductive component 130 is double-side conductive foam 132 or tape. In one embodiment, for example, and as shown particularly in FIGS. 10, 11, and 14, the double-side conductive foam 132 or tape may be sandwiched between a bottom surface 138 of the outer covering 112 and a top surface 140 of the electronic display 106. In such embodiments, as shown particularly in FIG. 14, the signal path, as indicated by arrows 123, travels through the electronic display 106 first and then through the printed circuit board 128. Thus, as shown in FIGS. 10, 11, and 14, in certain embodiments, the electronic display 106 can be connected through the printed circuit board 128 by anisotropic conductive film (ACF) bonding. As used herein, ACF bonding generally refers to a lead-free and environmentally friendly adhesive interconnect film system or paste that can be used to make electrical and mechanical connections. Further, as shown, conductive line(s) 142 connected to the biometric sensor electrode(s) 122, 124 and the conductive component 130 are connected to the printed circuit board 128 to deliver the sensing signal to the electronics package 110.

Figure 15:
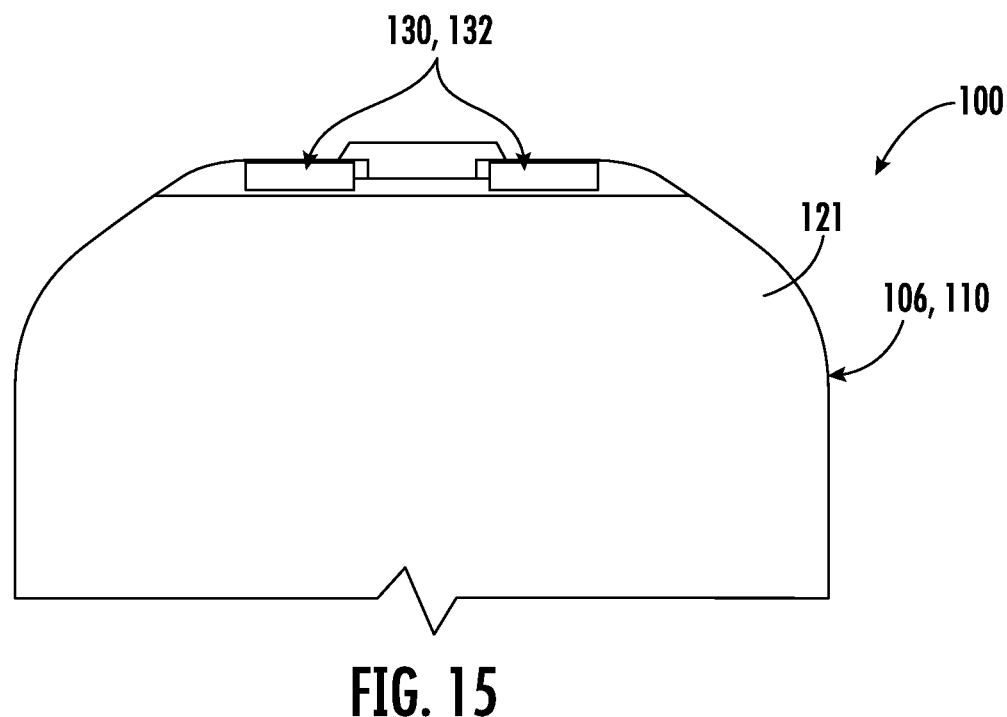
FIG. 15 provides top view of the double-side conductive tape or the double-side conductive foam arranged on the electronic display of the wearable computing device according to another embodiment of the present disclosure.
Figure 16:
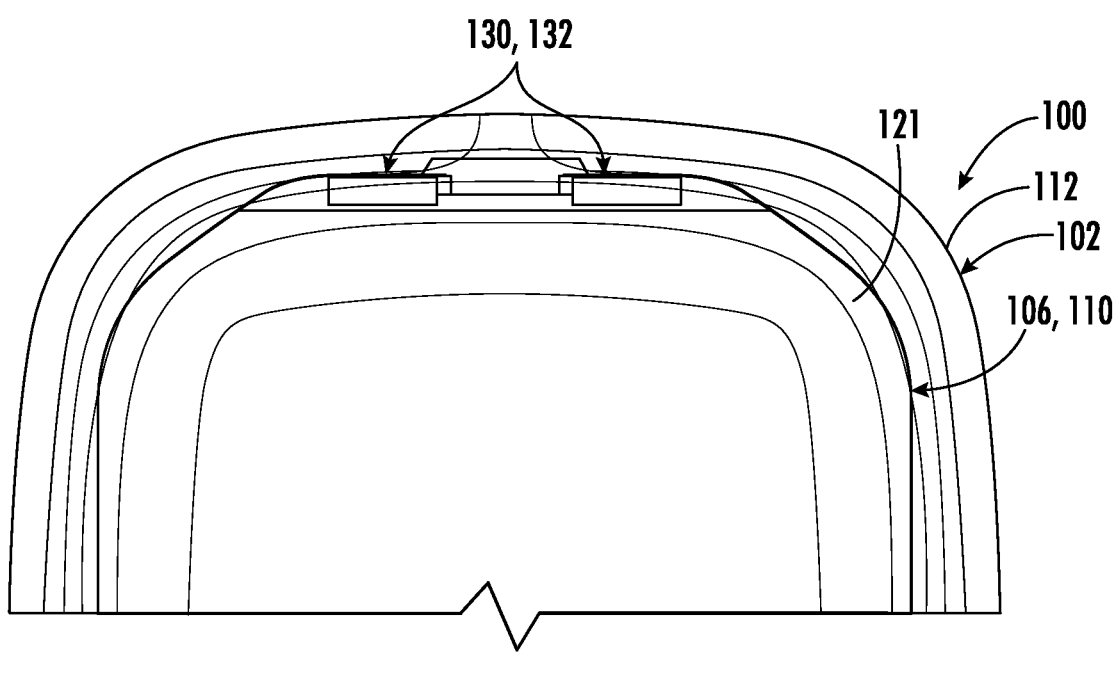
FIG. 16 provides top view of the wearable computing device according to another embodiment of the present disclosure, particularly illustrating double-side conductive tape or foam placed on a top surface of the printed circuit board.
Figure 17:
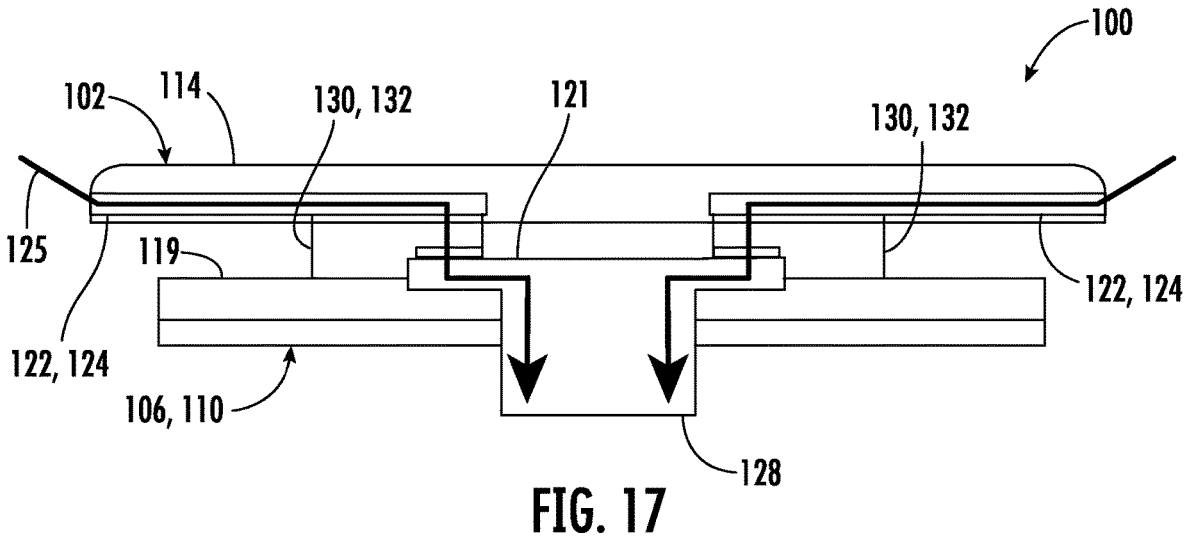
FIG. 17 provides a cross-sectional view of the wearable computing device according to one embodiment of the present disclosure, particularly illustrating first and second biometric sensor electrodes arranged on opposite sides of a printed circuit board and placed on a top surface of the printed circuit board.

In alternative embodiments, as shown in FIGS. 15-17, the double-side conductive foam 132 or tape may be placed on a top surface 121 of the printed circuit board 128. In such embodiments, as shown, the electronic display 106 becomes part of the printed circuit board 128 (i.e., its top surface). Accordingly, as shown particularly in FIG. 17, the double-side conductive foam 132 or tape is configured to sit on the top surface 121 of the printed circuit board 128 (e.g., on the wing side top surface of the electronic display 106). In such embodiments, as shown particularly in FIG. 17, the signal path, as indicated by arrows 125, travels by the electronic display 106 and directly through the printed circuit board 128.

Figure 19:
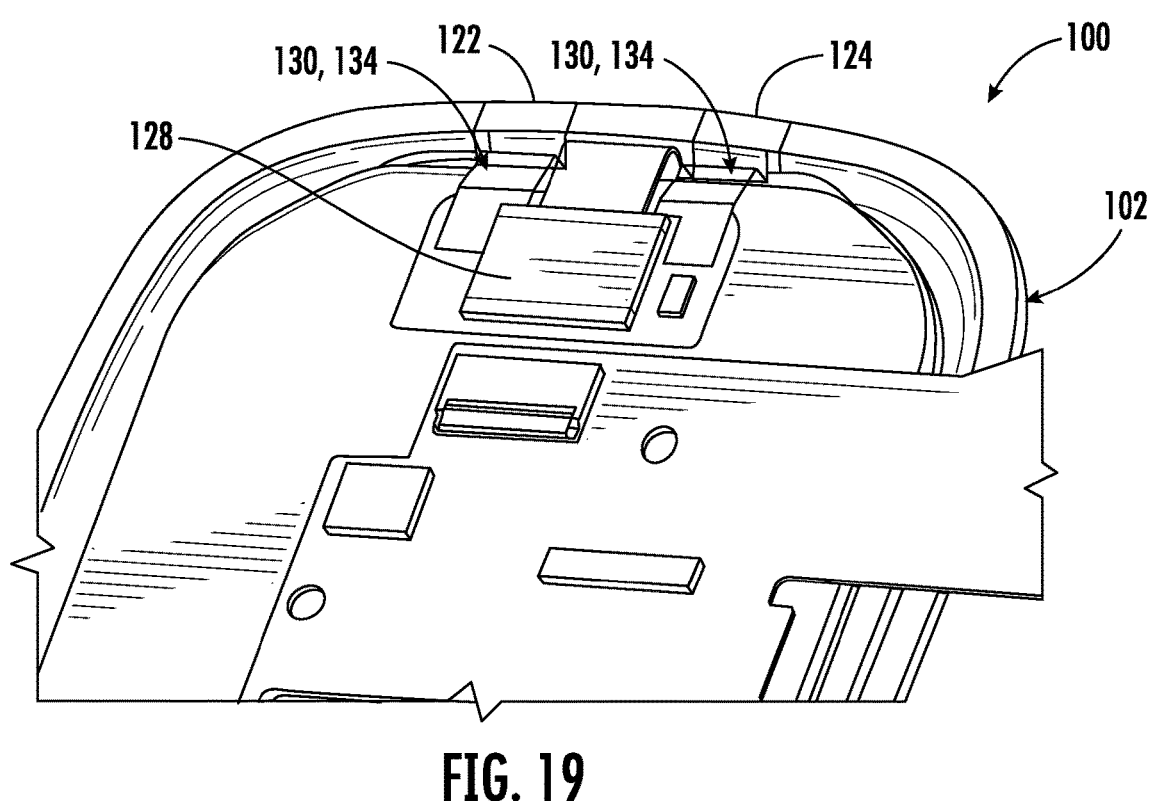
FIG. 19 provides a partial, perspective view of a rear-side of a wearable computing device according to one embodiment of the present disclosure, particularly illustrating first and second biometric sensor electrodes electrically connected to a printed circuit board via single-side conductive tape.
Figure 20:
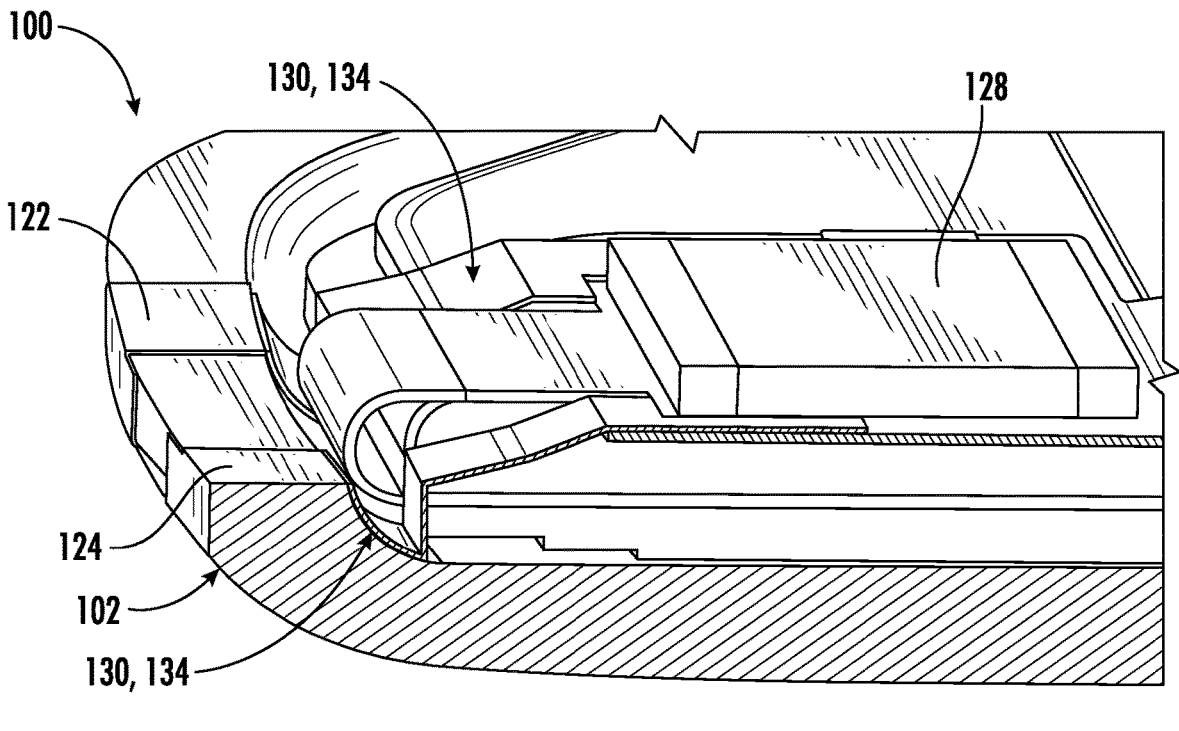
FIG. 20 provides a partial, perspective view of another rear-side of a wearable computing device according to one embodiment of the present disclosure, particularly illustrating first and second biometric sensor electrodes electrically connected to a printed circuit board via single-side conductive tape.

Alternatively, as shown in FIGS. 19-20, the conductive component 130 is double-side conductive tape 134 or film. In such embodiments, as shown, the conductive tape 134 or film may be applied directly to the biometric sensor electrode(s) 122, 124 to electrically connect the biometric sensor electrode(s) 122, 124 to the printed circuit board 128. More particularly, as shown, the biometric sensor electrode(s) 122, 124 wrap around the side edge of the outer covering 112 to the internal volume 118 such that a first end of the conductive tape 134 or film can be secured to an end of the biometric sensor electrode(s) 122, 124 and an opposing end of the conductive tape 134 or film can be secured directly to the printed circuit board 128 (or to a conductive component in direct contact with the printed circuit board 128). Furthermore, in such embodiments, the conductive component 130 may include separate conductive tapes or a single conductive tape with two conductive lines.

Figures 21, 22:
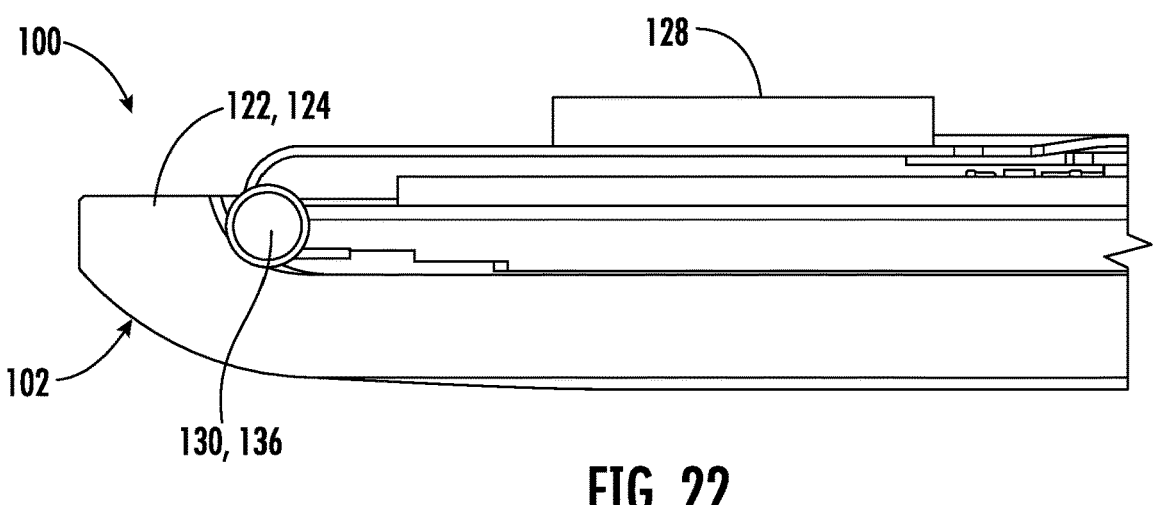
FIG. 21 provides a partial, side view of a wearable computing device according to one embodiment of the present disclosure, particularly illustrating first and second biometric sensor electrodes electrically connected to a printed circuit board via single-side conductive tape and conductive adhesive.
FIG. 22 provides a partial, rear-side view of the wearable computing device of FIG. 16, particularly illustrating first and second biometric sensor electrodes electrically connected to a printed circuit board via single-side conductive tape and conductive adhesive.

Referring now to FIG. 21, the conductive component 130 is ACF (anisotropic conductive film or paste) bonding 135. In such embodiments, as an example, the ACF bonding 135 can be applied directly to the biometric sensor electrode(s) 122, 124 to electrically connect the biometric sensor electrode(s) 122, 124 to the printed circuit board 128. In such embodiments, the ACF bonding 135 can be used alone or in combination with the conductive tape 134 or film to provide additional support. Thus, in such embodiments, as shown at step (1), the ACF bonding 135 can be connected to the biometric sensor electrode(s) 122, 124, which are located on a hard glass surface. As shown at step (2), the electronics display 106 can then be laminated on top of the ACF bonding 135. Moreover, as shown at step (3), the ACF bonding 135 can be connected to the printed circuit board 128 or any suitable location that can ultimately be electrically connected to the printed circuit board 128. Such a connection can be completed using, for example, soldering, connectors, springs, fasteners, or similar.

Figure 23:
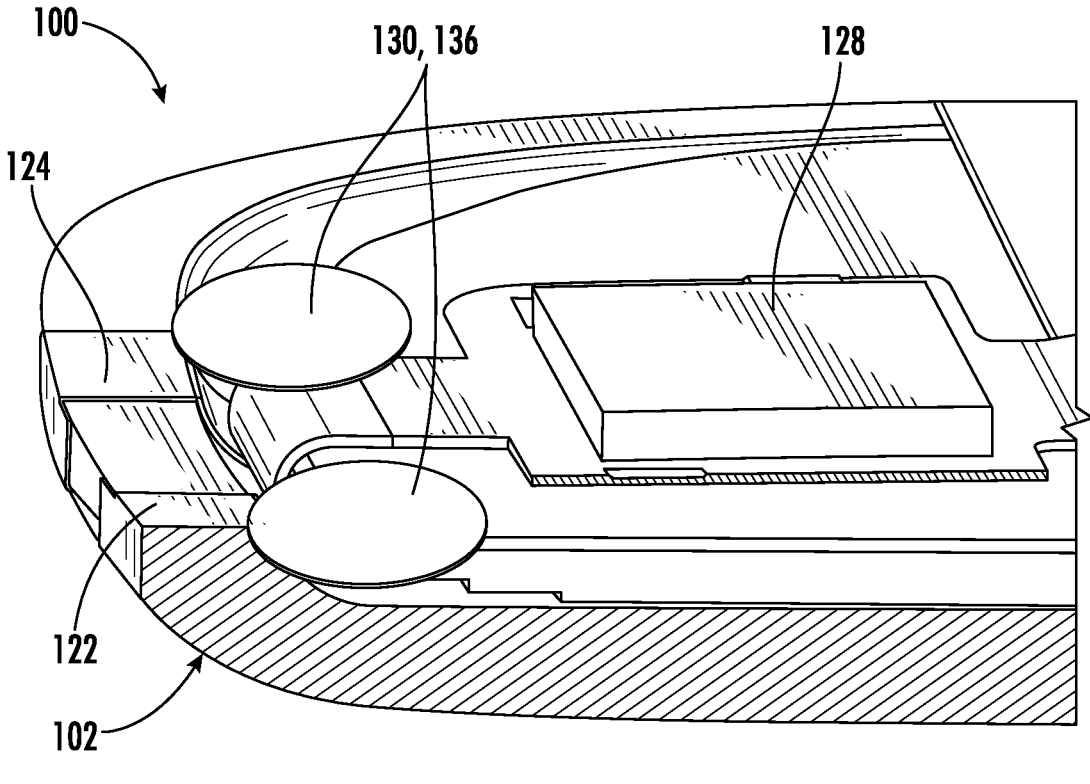
FIG. 23 provides a partial, side view of a wearable computing device according to one embodiment of the present disclosure, particularly illustrating first and second biometric sensor electrodes electrically connected to a printed circuit board via anisotropic conductive film.

In still another embodiment, as shown in FIGS. 22-23, the conductive component 130 is a conductive adhesive 136 through direct contact, such as, for example, silver epoxy. In still further embodiments, the conductive component 130 may be single-side conductive tape, single-side conductive foam, anisotropic conductive film, or combinations thereof. In further embodiments, any suitable connection is possible to connect such components together to define the desired low-resistance path.

In still further embodiments, as shown in FIGS. 10 and 11, the wearable computing device 100 may further include a contact pad 144 arranged between the double-side conductive foam 130, 132 or tape and the top surface 140 of the electronic display 106. In such embodiments, for example, the contact pad 144 may be a thin metal film. Thus, as shown, the printed circuit board 128 is electrically coupled to an edge of the contact pad 144, e.g., through conductive line(s) 142. In further embodiments, the printed circuit board 128 may be arranged adjacent to the contact pad 144 and may be electrically connected to a bottom surface of the contact pad 144 such that the conductive line(s) 142 can be omitted.

Referring now to FIG. 24, a flow diagram of one embodiment of a method 200 of assembling a wearable computing device is provided. In an embodiment, for example, the wearable computing device may be any suitable wearable computing device such as the wearable computing device 100 described herein with reference to FIGS. 1-23. In general, the method 200 is described herein with reference to the wearable computing device 100 of FIGS. 1-24. However, it should be appreciated that the disclosed method 200 may be implemented with any other suitable wearable computing device having any other suitable configurations. In addition, although FIG. 24 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown at (202), the method 200 includes providing an outer covering defining an outer-most top surface and an outer perimeter, an inner surface of the outer covering defining an internal volume. For example, FIGS. 2-7 generally illustrate an embodiment of the outer covering 112 according to the present disclosure. Referring back to FIG. 24, as shown at (204), the method 200 includes positioning a first portion of at least one biometric sensor electrode on the outer-most top surface of the outer covering and wrapping a second portion of the at least one biometric sensor electrode around one or more side edges of the outer covering such that the second portion is within the internal volume. For example, FIGS. 2-7 generally illustrate an embodiment of a first portion of the biometric sensor electrodes 122, 124 on the outer-most top surface 114 of the outer covering 112. Furthermore, as shown particularly in FIGS. 5, 7, 15, 16, 18, and 19, a second portion of the biometric sensor electrodes 122, 124 wrap around one or more side edges of the outer covering 112 such that the second portion is within the internal volume 118 of the wearable computing device 100 according to the present disclosure.

Referring back to FIG. 24, as shown at (206), the method 200 includes placing an electronic display and an electronic display module connector within the internal volume. As shown at (208), the method 200 includes arranging a printed circuit board within the internal volume adjacent to the electronic display.

As shown at (210), the method 200 includes electrically connecting the biometric sensor electrode(s) to the printed circuit board through the electronic display module connector via at least one conductive component. In such embodiments, the conductive component(s) defines a low-resistance path. For example, in an embodiment, as shown in FIGS. 10-14, electrically connecting the biometric sensor electrode(s) 122, 124 to the printed circuit board 128 through the electronic display module connector 110 includes placing the conductive component(s) 130 between the bottom surface 138 of the outer covering 112 and a top surface of 119 the electronic display 106. In alternative embodiments, as shown in FIG. 15-17, electrically connecting the biometric sensor electrode(s) 122, 124 to the printed circuit board 128 through the electronic display module connector 110 includes placing the conductive component(s) 130 on a top surface 121 of the printed circuit board 128. In addition, in certain embodiments, as described herein, the conductive component(s) 130 may be double-side conductive tape, double-side conductive foam, single-side conductive tape, single-side conductive foam, conductive adhesive, anisotropic conductive film, or combinations thereof. In an embodiment, for example, wherein the conductive component 130 is the double-side conductive tape or the double-side conductive foam, the method 200 may include laminating the outer covering 112, the double-side conductive tape or the double-side conductive foam 132, and the biometric sensor electrode(s) 122, 124 together.

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A wearable computing device, comprising:
an outer covering defining an outer-most top surface and an outer perimeter;
an internal volume defined, at least in part, by an inner surface of the outer covering;
an electronic display and an electronic display module connector arranged within the internal volume;
at least one biometric sensor electrode positioned on the outer-most top surface of the outer covering and wrapping around one or more side edges of the outer covering to the internal volume;
a printed circuit board arranged within the internal volume;
a conductive component electrically connecting the at least one biometric sensor electrode to the printed circuit board through the electronic display module connector; and
a contact pad arranged between the conductive component and a top surface of the electronic display,
wherein the at least one biometric sensor electrode wraps around the one or more side edges of the outer covering to the internal volume such that a first end of the conductive component is secured to an end of the at least one biometric sensor electrode and an opposing end of the conductive component is secured directly to one of the printed circuit board or a conductive component in direct contact with the printed circuit board.

2. The wearable computing device of claim 1, further comprising a seal arranged along the outer perimeter of the outer covering, the internal volume being defined by the inner surface of the outer covering and an inner edge of the seal, the at least one biometric sensor electrode wrapping around the one or more side edges of the outer covering and the inner edge of the seal to the internal volume.

3. The wearable computing device of claim 1, wherein the conductive component comprises at least one of double-side conductive tape, double-side conductive foam, single-side conductive tape, single-side conductive foam, conductive adhesive, anisotropic conductive film, or combinations thereof.

4. The wearable computing device of claim 3, wherein the conductive component between the at least one biometric sensor electrode and the printed circuit board comprises the double-side conductive tape or the double-side conductive foam, the double-side conductive tape or the double-side conductive foam being sandwiched between a bottom surface of the outer covering and the top surface of the electronic display.

5. The wearable computing device of claim 3, wherein the conductive component between the at least one biometric sensor electrode and the printed circuit board comprises the double-side conductive tape or the double-side conductive foam, the double-side conductive tape or the double-side conductive foam being on a top surface of the printed circuit board.

6. The wearable computing device of claim 1, wherein the contact pad comprises a thin metal film.

7. The wearable computing device of claim 1, wherein the printed circuit board is electrically coupled to an edge of the contact pad.

8. The wearable computing device of claim 1, wherein the printed circuit board is arranged adjacent to the contact pad and is electrically connected to a bottom surface of the contact pad.

9. The wearable computing device of claim 1, wherein the at least one biometric sensor electrode comprises, at least, a first biometric sensor electrode and a second biometric sensor electrode, the first and second biometric sensor electrodes being spaced apart by a gap.

10. The wearable computing device of claim 9, wherein the first and second biometric sensor electrodes are arranged on the same side of the printed circuit board.

11. The wearable computing device of claim 9, wherein the first and second biometric sensor electrodes are arranged on opposite sides of the printed circuit board.

12. The wearable computing device of claim 1, wherein the at least one biometric sensor electrode comprises a physical vapor deposition (PVD) sensor pad.

13. The wearable computing device of claim 1, wherein the outer covering is constructed of at least one of glass, polycarbonate, or acrylic.

14. The wearable computing device of claim 1, wherein the at least one biometric sensor electrode comprises at least one of an electrocardiogram (ECG) sensor or an electrodermal activity (EDA) sensor.

15. A method of assembling a wearable computing device, the method comprising:

providing an outer covering defining an outer-most top surface and an outer perimeter, an inner surface of the outer covering defining an internal volume;

positioning a first portion of at least one biometric sensor electrode on the outer-most top surface of the outer covering and wrapping a second portion of the at least one biometric sensor electrode around one or more side edges of the outer covering such that the second portion is within the internal volume;

placing an electronic display and an electronic display module connector within the internal volume;

arranging a printed circuit board within the internal volume adjacent to the electronic display; and electrically connecting the at least one biometric sensor electrode to the printed circuit board through the electronic display module connector via at least one conductive component, wherein, when the at least one biometric sensor electrode is wrapped around the one or more side edges of the outer covering to the internal volume, electrically connecting the at least one biometric sensor electrode to the printed circuit board through the electronic display module connector via at least one conductive component further comprises securing a first end of the conductive component to an end of the at least one biometric sensor electrode and securing an opposing end of the conductive component directly to one of the printed circuit board or a conductive component in direct contact with the printed circuit board, and laminating the outer covering, the at least one conductive component, and the at least one biometric sensor electrode together.

16. The method of claim 15, wherein electrically connecting the at least one biometric sensor electrode to the electronic display module connector through the printed circuit board further comprises placing the at least one conductive component between a bottom surface of the outer covering and a top surface of the electronic display or on a top surface of the printed circuit board, the at least one conductive component comprising at least one of double-side conductive tape, double-side conductive foam, single-side conductive tape, single-side conductive foam, conductive adhesive, anisotropic conductive film, or combinations thereof.

17. The method of claim 16, further comprising placing a contact pad adjacent the double-side conductive tape or the double-side conductive foam.

18. The method of claim 17, further comprising electrically connecting the printed circuit board to an edge of the contact pad.

* * * * *